US00PP31155P2

(12) United States Plant Patent
Hansen

(10) Patent No.: US PP31,155 P2
(45) Date of Patent: Dec. 3, 2019

(54) ***EUCOMIS* PLANT NAMED 'AFRICAN NIGHT'**

(50) Latin Name: ***Eucomis comosa* (Houtt.) *Wehrh***
Varietal Denomination: African Night

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/350,796

(22) Filed: Jan. 14, 2019

(51) Int. Cl.
*A01H 5/02* (2018.01)
*A01H 6/12* (2018.01)

(52) U.S. Cl.
USPC ..... Plt./263.1

(58) Field of Classification Search
USPC ..... Plt./263.1
CPC ..... A01H 5/02; A01H 6/12
See application file for complete search history.

*Primary Examiner* — Annette H Para

(57) ABSTRACT

A new and distinct *Eucomis* plant named 'African Night' with rounded-mound habit of glossy, finely serrulate, strap-like, arching leaves emerging rich burgundy colored and developing to olive green. Beginning in mid-summer and lasting for about four weeks, the plants produce tall racemes with dense flowers of rosy pink. 'African Night' is winter-hardy to USDA zone 6 and useful as a specimen landscape plant, en masse, as a container plant or as a cut flower.

2 Drawing Sheets

Latin name and variety denomination of the plant:
Botanical classification: *Eucomis comosa* (Houtt.) Wehrh.
Variety denomination: 'African Night'.

STATEMENT REGARDING PRIOR DISCLOSURES UNDER 37 CFR 1.77(B)(6)

The first public disclosure of the claimed plant was made by Walters Gardens, Inc. on Feb. 1, 2018 when the claimed plant was displayed as a photograph with short description on a website owned and operated by Walters Gardens, Inc., and the initial sale of the new plants was on Jul. 16, 2018, also by Walters Gardens, Inc. who obtained the plant and all information relating thereto, from the inventor. No plants of *Eucomis* 'African Night' have been sold, in this country or anywhere in the world, nor has any disclosure of the new plant been made, more than one year prior the filing date of this application, and such disclosure within one year was either derived directly or indirectly from the inventor.

BACKGROUND AND ORIGIN OF THE PLANT

There are twelve recognized species within the genus *Eucomis* in the Asparagaceae family. The present invention relates to a new and distinct hosta plant, *Eucomis* 'Africa Night' hereinafter also referred to as the new plant or the cultivar name, 'Africa Night'. *Eucomis* 'Africa Night' was hybridized at a wholesale nursery in Zeeland, Mich., USA in Jul. 16, 2009 as a cross between *Eucomis comosa* 'Reuben' (not patented) as the female or seed parent, and *Eucomis comosa* 'Sparkling Burgundy' (not patented) as the male or pollen parent. The new plant is a single seedling selection among several in that cross identified by the breeder code 9-6-01 through the trial process. The new plant has been asexually propagated by leaf accessions and separation of the bulbs at the same nursery in Zeeland, Mich., USA since 2014, with the resultant asexually propagated plants having retained all the same traits as the original plant.

BRIEF SUMMARY OF THE PLANT

*Eucomis* 'African Night' is a distinct and new variety of Pineapple Lily. The new plant can be compared with the parent cultivars, 'EUW061' U.S. Plant Pat. No. 23,699 and 'Safari Adventure' U.S. Plant patent application Ser. No. 16/350,797. 'EUW061' are comparable to the new variety but produce flowers that change in color intensity through maturity, and the foliage does not get the rich burgundy as the new plant is emerging. 'Sparkling Burgundy' is slightly more upright in foliage and the flowers open ivory white and change to a rosy pink with maturity. 'Reuben' is shorter in flower stem, and the flowers are smaller with more cranberry coloration and the leaves are more green and do not emerge with the rich burgundy coloration. 'Safari Adventure' has foliage with less burgundy coloration and the flowers change color with maturity.

*Eucomis* 'African Night' is distinct from all cultivars known to the inventor in the following combined traits:

1. Bulbous winter-hardy perennial with strap-shaped arching leaves emerging from the ground;
2. Foliage color begins emerging in the spring with deep burgundy coloring;
3. Leaves are glossy above and below, the margins are finely serrulate and flat to boat-shaped;
4. Each mature bulb produces a tall raceme with dense flowers that open rosy pink;
5. Winter-hardy to USDA zone 6.

BRIEF DESCRIPTION OF THE DRAWINGS

The photographs of the new plant demonstrate the overall appearance of the new plant, including the unique traits grown in full-sun trial gardens in Zeeland, Mich. The colors are as accurate as reasonably possible with color reproductions. Ambient light spectrum, temperature, source and direction may cause the appearance of minor variation in color.

DETAILED BOTANICAL DESCRIPTION

Figure 1:
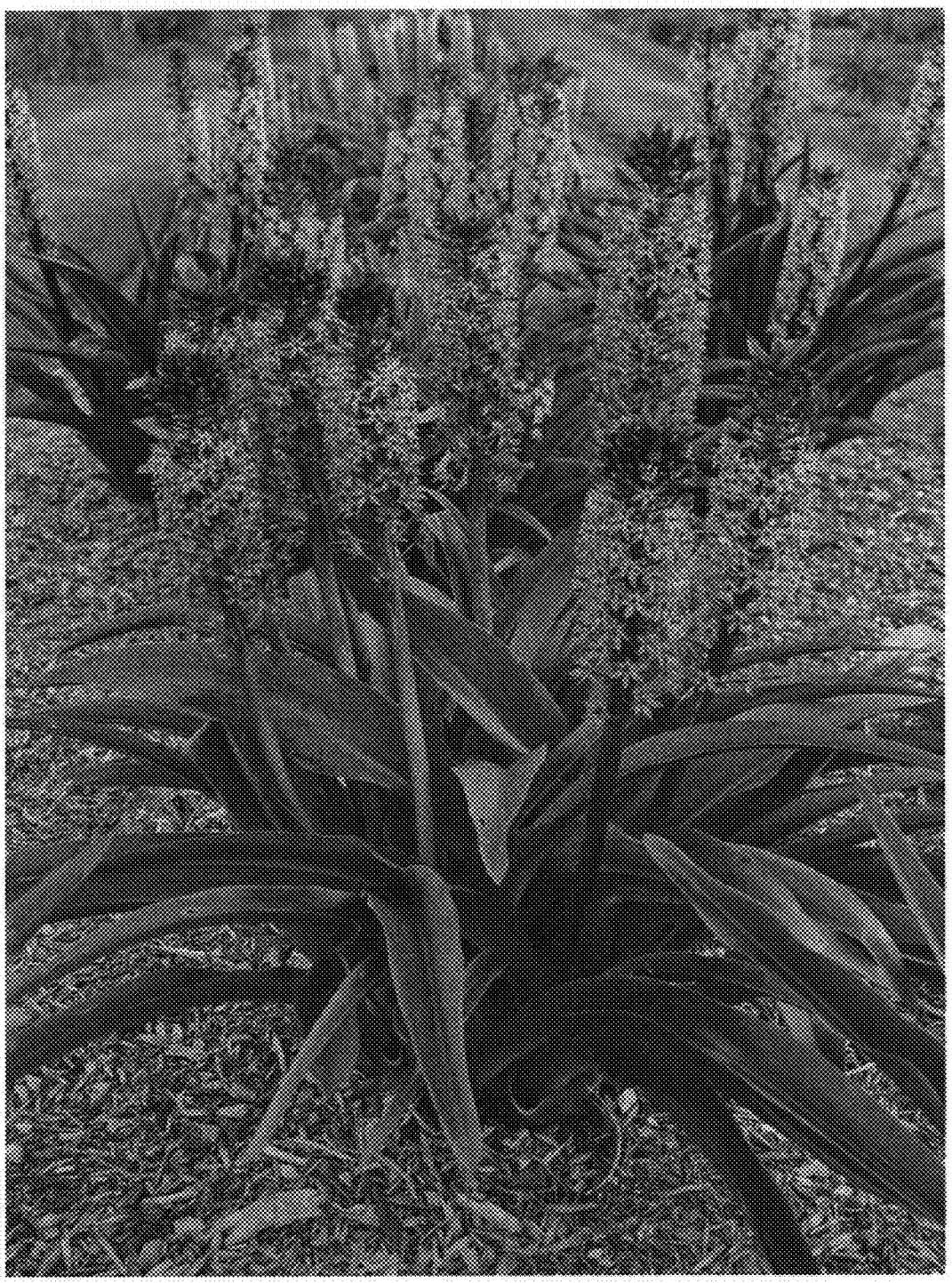
FIG. 1 shows the plant habit of an eight-year-old plant.
Figure 2:
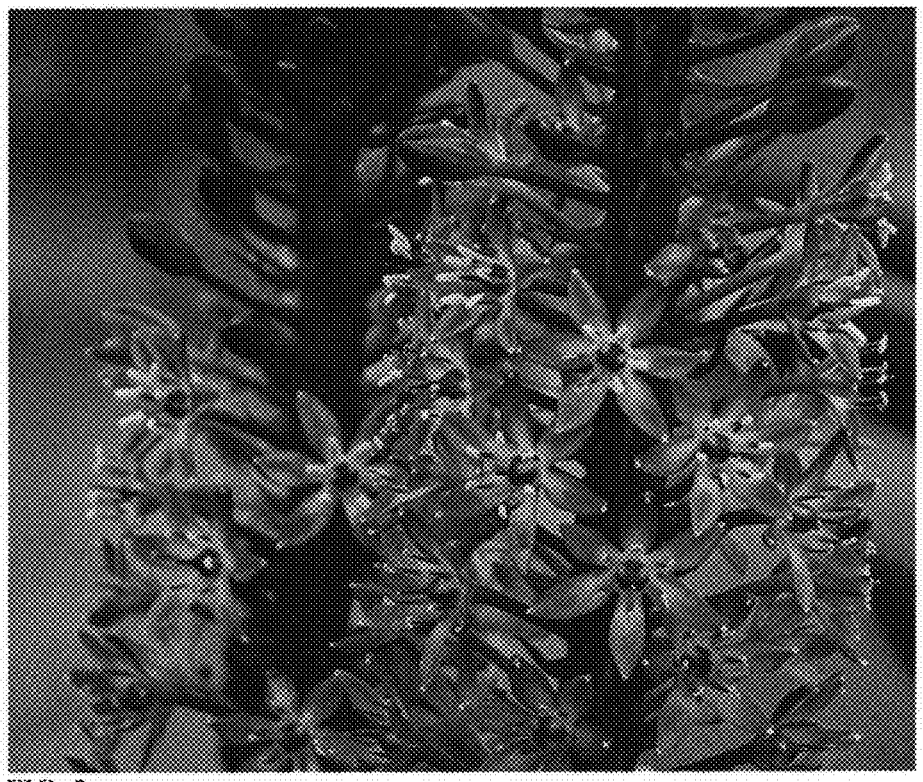
FIG. 2 shows a close-up of the flowering scape with buds and rosy pink flowers.
Figure 3:
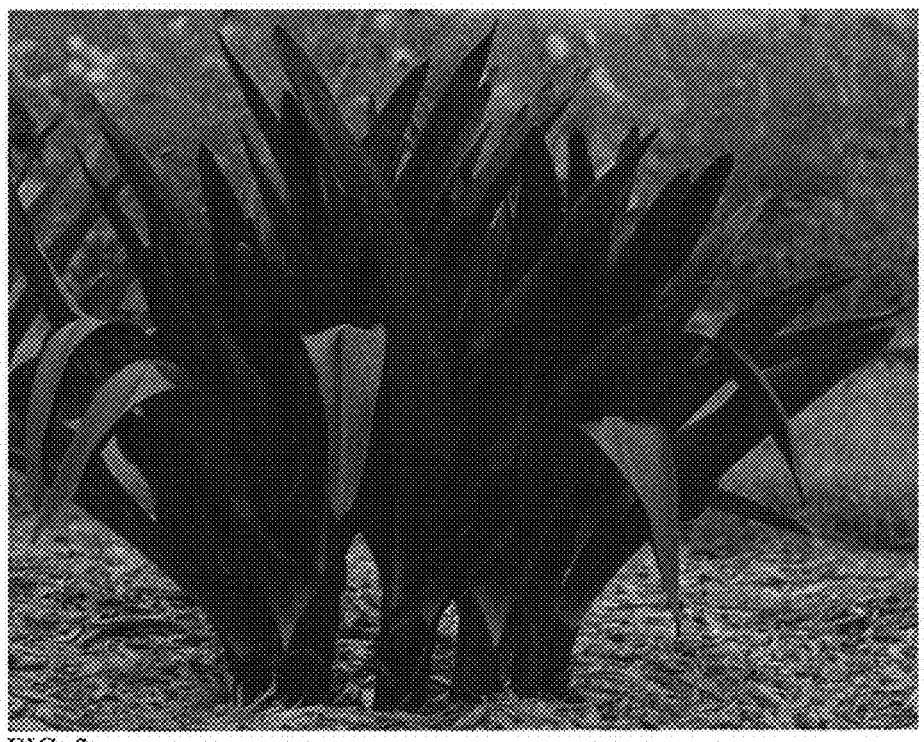
FIG. 3 shows the emerging foliage with rich burgundy coloration.

The following descriptions and color references are based on the 2015 edition of The Royal Horticultural Society Colour Chart except where common dictionary terms are used. The new plant, *Eucomis* 'African Night', has not been observed under all possible environments. The phenotype may vary slightly with different environmental conditions, such as temperature, light, fertility, moisture and maturity levels, but without any change in the genotype. The following observations and size descriptions are of an eight-year-old plant in a full-sun trial garden in Zeeland, Mich. with supplemental water and fertilizer.

Botanical classification: *Eucomis comosa;*

Parentage: 'Reuben' as the female parent, and the male parent is 'Sparkling Burgundy';

Propagation: Leaf accessions and separation of the bulbs;

Time to initiate bulblets from leaf accessions: About three months during the winter growing season;

Growth rate: Moderate;

Crop time: About two growing season to produce flowering size bulbs from a 25 mm liner;

Rooting habit: Normal, fleshy, lightly branching; color between RHS NN155D and RHS 158A depending on soil type and root age;

Plant shape and habit: Hardy herbaceous perennial with basal rosette of leaves emerging from about nine bulbs producing a more or less symmetrical, rounded-mound of leaves and upright racemes of compact flowers and topknot of small leaves;

Plant size: Foliage height about 58.0 cm above soil line to the top of the leaves and about 94.0 cm wide at the widest point slightly above the soil line;

Bulb: Turbinate; tunicate; about 5.5 cm diameter and 3.5 cm tall; color variable with portions nearest RHS NN155C and other portions between RHS 175A and RHS 175B;

Foliage description: Acaulescent arising from bulb; linear; glabrous, lustrous abaxial and adaxial; lance, with narrowly acute apex and truncate base; margin finely serrulate; blades generally flat to navicular; without twisting; arching with maturity;

Leaf blade size: To about 68.0 cm long, 8.2 cm wide near base; average about 58.0 cm long, 6.5 cm wide;

Leaf blade color: Early emerging adaxial nearest RHS 187A, emerging abaxial nearest RHS 187A with base nearest RHS NN155B and portion just above base nearest RHS N186D; mature adaxial nearest RHS N138B with variable blushing of nearest RHS 187B and maculate with spots of about 1.0 mm diameter nearest RHS N186B concentrated toward base, mature abaxial between RHS 138B and RHS 138A with slight blushing of nearest RHS 187B and maculate with spots of about 1.0 mm diameter nearest RHS N186B concentrated toward base;

Veins: Parallel, not discernable; with fleshy thick midrib;

Veins color: Emerging adaxial midrib nearest RHS N186C, abaxial emerging midrib nearest blend between RHS N186D and RHS 186A; mature adaxial midrib nearest RHS 191C, mature abaxial midrib nearest RHS 143C;

Topknot: With ten to fifteen small leaves at apex of raceme; about 3.5 cm tall and 4.0 cm wide; topknot leaves ovate with acute apex and truncate base, margin entire; cupped; leaves average about 25.0 mm long and 11.0 mm wide;

Topknot leaf color: Adaxial and abaxial blend of nearest RHS 187A and nearest RHS 146B;

Inflorescence: Raceme; flowers radially arranged, non-secund; flowering portion about 42.0 cm long and 12.0 cm wide; racemes effective with flowers beginning late July for about four weeks in Michigan landscape or about two to three weeks as a cut flower depending on storage conditions; about 150 flowers per raceme;

Buds one day prior to opening: Ellipsoidal with rounded apex and base; 14.0 mm long, with and about 8.0 mm diameter;

Bud color: Nearest blend between RHS 182D and RHS 186D;

Flowers: Perfect; single; regular; actinomorphic; whorl; persistent; attitude outwardly to slightly upright; about 35.0 mm wide and 18.0 mm long, decreasing distally; individually persist for about two weeks;

Flower fragrance: Faintly sweet;

Tepal: Six; fleshy; glabrous; margin entire; obtuse; acute apex and truncate base; approximately 14.0 mm long and about 8.0 mm wide toward apex;

Tepal color: Adaxial nearest RHS N74D, abaxial nearest RHS N74D with longitudinal center having undertone of nearest RHS 146C;

Gynoecium: Single; tri-carpelled; 12.0 mm long; exserted;

*Style*.—Single; cylindrical; approximately 6.5 mm long, 1.0 mm diameter at base; color nearest N186C.

*Stigma*.—Flattened; about 0.5 mm across; color nearest RHS NN187D.

*Ovary*.—Superior; globose; about 5.5 mm long and 3.5 mm diameter; rounded apex and truncate base; color nearest RHS 70A.

Androecium:

*Filaments*.—Typically six; adnate to inner corolla and connate in basal 3.0 mm; cylindrical distally and flattened at base; approximately 10.0 mm long and 3.0 mm wide at base; color of base lighter than RHS 186D, distally nearest RHS 70A.

*Anthers*.—Oblanceolate; dorsifixed, longitudinal; about 4.0 mm long and 2.0 mm wide; color nearest RHS 1A.

*Pollen*.—Abundant; elliptic, less than 0.1 mm long; color nearest RHS 4B.

Peduncle: Terete; usually one per mature division and eight per plant; lustrous, glabrous; upwardly; to about 86.0 cm tall, and about 20.0 mm in diameter at base; average about 81.0 cm and 18.0 mm diameter;

Peduncle color: When first flowering between RHS N186D and RHS 186A, as flowering matures developing undertone of nearest RHS 146D;

Pedicel: Glabrous; lustrous; cylindrical; slightly upwardly; approximately 24.0 mm long and 2.0 mm diameter;

Pedicel color: Between RHS 186A and N186C;

Foliar bract: Each flower subtended by a single bract, deltoid; acute apex; truncate clasping base; entire margin; about 10.0 mm long and 8.0 mm across base; color nearest RHS 146D with blushing of nearest RHS 187B;

Fruit: Ellipsoidal; with acute apex and truncate base; tri-valved dehiscent capsule; about 8.0 cm long and 8.0 mm across; color when mature nearest RHS 177A;

Seed: Globose; about 2.0 mm long and 1.5 mm wide; color nearest RHS 202A;

Disease tolerance and resistance: The new plant has not shown any resistance to pests and diseases common to Pineapple Lilies. The plant grows best and shows best coloration with plenty of moisture, adequate drainage and full sun. Winter hardiness has been tested in USDA zone 6. Other disease resistance is typical of that of other *Eucomis*.

It is claimed:

1. A new and distinct ornamental *Eucomis* cultivar named 'African Night' as herein described and illustrated.

* * * * *